United States Patent [19]
Kurotsu et al.

[11] Patent Number: 5,510,315
[45] Date of Patent: Apr. 23, 1996

[54] FRESHNESS RETENTIVE FOR CUT FLOWERS

[75] Inventors: Takahiro Kurotsu; Hiroyuki Itoh; Sadatoshi Sakuma, all of Odawara, Japan

[73] Assignee: Meiji Milk Products Company Limited, Japan

[21] Appl. No.: 87,812

[22] PCT Filed: Nov. 6, 1992

[86] PCT No.: PCT/JP92/01439

§ 371 Date: Jul. 8, 1993

§ 102(e) Date: Jul. 8, 1993

[87] PCT Pub. No.: WO93/08685

PCT Pub. Date: May 13, 1993

[30] Foreign Application Priority Data

Nov. 8, 1991 [JP] Japan ................... 3-293467

[51] Int. Cl.$^6$ ...................................................... A01N 3/02
[52] U.S. Cl. .............................................................. 504/115
[58] Field of Search ................................... 504/114, 115

[56] References Cited

U.S. PATENT DOCUMENTS

| | | | |
|---|---|---|---|
| 2,042,974 | 6/1936 | Weissflog | 504/115 |
| 2,805,137 | 9/1957 | Clopton | 504/115 |
| 3,112,192 | 11/1963 | Feichtmeir et al. | 504/115 |

FOREIGN PATENT DOCUMENTS

| | | |
|---|---|---|
| 2-23521 | 1/1990 | Japan. |
| 1297258 | 3/1970 | United Kingdom. |
| 2189676 | 11/1987 | United Kingdom. |

OTHER PUBLICATIONS

Halevy and Kofranek, 1977, "Silver treatment of carnation flowers for reducing ethylene damage and extending longevity", J. Amer. Soc. Hort. Sci. 102(1):76–77.

Veen, 1979, "Effects of silver on ethylene synthesis and action in cut carnations", Planta 145:467–470.

Veen and van de Geijn, 1978, "Mobility and ionic form of silver as related to longevity of cut carnations", Planta 140:93–96.

Zhao, 1987, "Preservatives for cut flowers", Chemical Abstracts, vol. 108, No. 17, Abstract No. 145467r.

Morrison, 1986, "Chemical could preserve ornamental crops longer", NTIS Tech Notes, vol. 1986, No. 1, Jan. 1986.

Fuji et al., 1971, "Oxidation catalysts for the oxidation of ethylene", Chemical Abstracts, vol. 77, No. 9, Abstract No. 61786x.

Shoyu, 1979, "Preserving plant leaves by contacting with aqueous solution containing nucleotide and/or nucleoside at specified concentration", Derwent WPI, AN 79–55636B & JP–B–54 017 670, Abstract.

Sylvestre and Paulin, 1987, "Accelerated ethylene production as related to changes in lipids and electrolyte leakage during senescence of petals of cut carnations", Chemical Abstracts, vol. 107, No. 15, Abstract No. 128997a.

Hakko, 1988, "Increasing harvest yield of monocious type cucumber by treating with agents for inhibiting ethylene biosynthesis and inhibiting ethylene action", Derwent WPI, AN 88–087058 & JP–A–63 036 716, Abstract.

Primary Examiner—Allen J. Robinson
Assistant Examiner—B. Bembenick
Attorney, Agent, or Firm—Pennie & Edmonds

[57] ABSTRACT

The present invention relates to a freshness retentive for cut flowers, which comprises a mixture of a silver compound and a primary amine and/or a nucleic acid-related substance and/or reaction products thereof. The silver compound is silver nitrate, silver acetate or silver phosphate; the primary amine is methylamine, ethylamine, monoethanolamine, tris(hydroxymethyl)aminomethane, 2-amino-2-methyl-1,3-propanediol, 2-amino-2-ethyl-1,3-propanediol, α-aminooxyacetic acid or aminoethoxyvinylglycine; and the nucleic acid-related substance is nucleic base, nucleoside, nucleotide, oligonucleotide, polynucleotide, purine derivative or pyrimidine derivative.

The present freshness retentive for cut flowers demonstrates an extremely excellent effect on cut flowers highly sensitive to ethylene, e.g. carnation, *Gypsophila elegans*, sweet pea, etc., as well as on cut flowers low sensitive to ethylene, e.g. chrysanthemum, rose, orchid, etc., for their freshness retention.

5 Claims, No Drawings

FRESHNESS RETENTIVE FOR CUT FLOWERS

INTRODUCTION

The present invention relates to a freshness retentive for cut flowers and more particularly to a freshness-retaining agent capable of maintaining the beauties of cut flowers in a fresh state over a long period of time by preventing during transportation the deterioration of freshness for cut flowers after being harvested and by preventing the deterioration of freshness caused by withering of petals and leaves or yellowing of leaves.

BACKGROUND OF THE INVENTION

The consumption of cut flowers such as chrysanthemum, rose, carnation, etc., is increasing year by year, and competition grows more and more keen in production and sales internationally or among domestic producing districts in recent years. Under the circumstances, the development in techniques of maintaining freshness for cut flowers, e.g. of long-lasting of flowers and helping flowers draw water, becomes increasingly important, and such demands are expected to be dissolved by a freshness-keeping agent for cut flowers.

A freshness-retentive for cut flowers (referred to as "retentive," hereinafter) consists of a pre-treatment agent and a post-treatment agent, each with different components and functions. The pre-treatment agent is employed for brief treatment of cut flowers before shipping to a retail shop in order to prolong preservation of flowers after being harvested and help flowers raise water, of which an anion complex of silver thiosulfate containing as a stabilizer a sulfite or the like is widely used at present (Japanese Patent Publication No. 23,521/90). The post-treatment agent comprises, as principal components, nutrients required for flowers (sugars, nitrogen, phosphoric acid, potassium, etc.), a germicide, a surface-active agent, etc., and this agent is to help prolong preservation for flowers on sale in a retail shop or flowers put in a vase for consumer's appreciation. The freshness retentive of the present invention belongs to the pre-treatment agent, but may also be employed as a post-treatment agent.

A wide variety of pharmaceutical agents have been available up to now as pre-treatment agents, among which the above-mentioned anion complex of silver thiosulfate is widely employed at present. Silver ions inhibit the action of ethylene, a plant hormone being influential as a factor of the aging (withering) of flowers. Spraying of carnation with silver nitrate prolongs the freshness of the flower. However, the speed of silver ions, if silver nitrate is absorbed through stems, is very slow in vessels and thus silver ions are difficult to reach the tissues of flower and leaf (Halevy, A. H. and Kofranek, A. M. (1977),"Silver treatment of carnation flowers for reducing ethylene damage and extending longevity." J. Amer. Soc. Hort. Sci., 102, 76–77). H. Veen, a Dutch scientist, prepared an anion complex of silver thiosulfate $[(Ag(S_2O_3)_2]^{3-}$ complex which is referred to as "silver thiosulfate complex," hereinafter) by mixing silver nitrate and sodium thiosulfate, in order to examine how the silver thiosulfate complex moved in the vessels of carnation. As a result, he found that the silver thiosulfate complex could move very rapidly in the vessels of carnation and prolong preservation of the flower to a great extent (Veen, H. and van de Geijn, S. C. (1978), "Mobility and ionic form of silver as related to longevity of cut carnations." Planta, 140, 93–96, Veen, H. (1977),"Effect of silver on ethylene synthesis and action in cut carnation." Planta, 145, 467–470). The silver thiosulfate complex is presently consumed in a great deal in all over the world because this complex, being capable of production at a low cost, exhibits a strong effect on retaining the freshness of cut flowers.

The silver thiosulfate complex widely used as described above, however, presents the following problems: (1) Silver is a heavy metal, so anxiety over environmental pollution is raised and (2) the silver thiosulfate complex does not have any effect on flowers low sensitive to ethylene, such as chrysanthemum, rose, orchid, etc., although the complex has a freshness retaining effect on flowers highly sensitive to ethylene, such as carnation, *Gypsophila elegans*, sweet pea, delphinium, etc. Particularly with respect to rose, no effective freshness retentive has been obtained still yet in spite of extensive investigations by researchers in all over the world.

DETAILED DESCRIPTION OF THE INVENTION

In order to solve the above problems inherent in the silver thiosulfate complex, the present inventors have made extensive investigations for obtaining a agent having a stronger effect on freshness retention for cut flowers than the silver thiosulfate complex. As a result, they found that a retentive, comprising a mixture of a silver complex and a primary amine and/or a nucleic acid-related substance and/or reaction products thereof, demonstrates a freshness retentive effect on cut flowers at a silver concentration lower than the silver thiosulfate complex, said effect being equal to or higher than that of the silver thiosulfate complex and with further enormous effect on cut flowers not susceptible to the freshness retentive effect of the silver thiosulfate complex, such as rose, chrysanthemum, orchid, etc.

The silver compound used in the preparation of the retentive of the present invention includes a monovalent silver compound, e.g. silver nitrate, silver phosphate, and silver acetate, among which silver nitrate has been widely used as an active ingredient of retentive since the old days and is most preferably used in the present invention, as well.

The primary amine used in the present invention includes e.g. methylamine, ethylamine, monoethanolamine, tris(hydroxymethyl)aminomethane (referred to as "tris," hereinafter), 2-amino-2-methyl-1,3-propanediol, 2-amino-2-ethyl-1, 3-propanediol, α-aminooxyacetic acid (AOA, $H_2N-O-CH_2COOH$), and aminoethoxyvinylglycine (AVG, $H_2NCH_2CH_2OCH=CHCHNH_2COOH$). Water-soluble primary amines not illustrated herein also fall within the scope of the present invention, as far as they are used as a retentive in accordance with the description of the present invention.

The nucleic acid-related substance used in the invention includes alkali-hydrolyzed or enzyme-digested nucleic acids (DNA, RNA) derived from animal or plant tissues, microorganisms, etc., as well as chemically synthesized polynucleotide, oligonucleotide, nucleotide, nucleoside, nucleic acid base, and compounds with a similar chemical structure, e.g. purine derivatives such as inosinic acid etc. Out of these, hydrolyzates of commercial yeast RNA extracted from a yeast microorganism are preferably used.

The retentive of the present invention is prepared by combining merely or reacting starting materials such as the above-mentioned silver compound, primary amine or nucleic acid-related substance. For the reaction thereof, conditions of manufacture such as mixing ratio (molar ratio), reaction temperature, pH, etc., are considerably variable, so a number of variations can be taken into consideration.

Examples of producing the retentive of the present invention are preferably as follows:

1) Retentive composed of a silver compound and a primary amine as starting materials:

In the case of using silver nitrate as a silver compound and tris as a primary amine, silver nitrate and tris, each in an aqueous solution, may be mixed simply or reacted. Silver nitrate and tris are allowed to react in an aqueous solution, thereby forming a complex (Analytical Chemistry, Vol. 47, No. 8, July 1975: 1465–1966). The amounts of silver nitrate and tris used are not particularly limited, preferably in the range of 0.004–0.400 mM Ag and 3–30 mM tris.

Silver nitrate or silver acetate, if used as a silver compound, is dissolved in an aqueous solution of tris, followed by dilution with water to a predetermined concentration.

The foregoing also applies to cases where the primary amine used is methylamine, ethylamine, monoethanolamine, 2-amino-2-methyl-1,3-propanediol, 2-amino-2-ethyl-1,3-propanediol, α-aminooxyacetic acid or aminoethoxyvinylglycine.

2) Retentive composed of a silver compound and a nucleic acid-related substance as starting materials:

The following applies to the case of using silver nitrate as a silver compound and RNA hydrolyzates as a nucleic acid-related substance.

The nucleic acid-related substance is prepared by hydrolysis of e.g. RNA under conditions not particularly limited.

RNA hydrolyzates are prepared by dissolving RNA in 0.1–2 N sodium hydroxide or potassium hydroxide, followed by hydrolysis thereof for 15 minutes to 24 hours at room temperature to 120° C. Subsequently, the hydrolyzates are neutralized with acetic acid etc. and are then dissolved in an aqueous solution of silver nitrate. If sparingly dissolved owing to the presence of proteins etc. mixed in the RNA, the hydrolyzates is preferably subjected to phenol treatment and subsequent ethanol precipitation. Before use, the retentive thus obtained is diluted to a silver concentration of 0.004–0.400 mM. Where nucleic acid base, nucleoside, nucleotide, oligonucleotide, polynucleotide, polynucleotide, purine derivative or pyrimidine derivative is used as a nucleic acid-related substance in place of RNA hydrolyzates, an aqueous solution thereof is mixed with an aqueous solution of silver nitrate, as well. If necessary, the solution is heated to promote dissolution of the nucleic acid-related substance.

3) Retentive composed of a silver compound, a primary amine, and a nucleic acid-related substance as starting materials:

The following applies to cases where silver nitrate is used as a silver compound, tris as a primary amine, and RNA hydrolyzates as a nucleic acid-related substance.

RNA hydrolysis is effected under conditions as described in 2) above. Alternatively, RNA is hydrolyzed with nucleic acid hydrolase such as RNase. The resultant RNA hydrolyzates are dissolved in water, an aqueous solution of tris, or an aqueous solution of diluted alkali. This solution of RNA hydrolyzates is mixed with an aqueous solution of silver nitrate, if necessary followed by neutralization with acetic acid etc., whereby the retentive of the present invention can be obtained. In case precipitates occur after the neutralization, the solution is heated for the precipitates to dissolve. Alternatively, the solution containing precipitates is separated by centrifugation into a supernatant and precipitates, and the supernatant is precipitated with ethanol, and these precipitates thus recovered are dissolved in tris, so that the retentive of the present invention can also be obtained. Before use, the original solution of retentive thus obtained is diluted to a silver concentration of 0.004–0.400 mM, and tris is added thereto. The foregoing also applies to cases where the primary amine used in place of tris is methylamine, ethylamine, monoethanolamine, 2-amino-2-methyl-1,3-propanediol, 2-amino-2-ethyl-1,3-propanediol, α-aminooxyacetic acid, or aminoethoxyvinylglycine.

The retentive of the present invention can incorporate, as necessary, a stabilizer such an alkali metal salt of sulfite etc., an antioxidant such as vitamin C etc., nutrients such as a sugar content, a nitrogen content, etc., a variety of surface-active agents, and a variety of germicides.

THE BEST MODE FOR CARRYING OUT THE INVENTION

The retentive of the present invention is further illustrated in detail with reference to Examples and Test Examples, which however are not intended to limit the scope of the present invention.

EXAMPLE 1

Preparation of a retentive composed of a silver compound and tris as starting materials 4.0 ml of 10 mM silver nitrate (manufactured by Nakarai Kagaku Co., Ltd.) and 50.0 ml of 200 mM tris (manufactured by Nakarai Kagaku Co., Ltd.), each in an aqueous solution, were mixed, followed by addition of water to adjust the total volume to 1 liter, whereby a retentive (0.040 mM silver and 10 mM Tris) was obtained.

EXAMPLE 2

Preparation of a retentive composed of a silver compound and nucleic acid hydrolyzates as starting materials 0.1 g of yeast-derived RNA (manufactured by Boehringer Mannheim BmbH; containing approximately 5% protein) or 0.1 g of salmon sperm-derived DNA (manufactured by Boehringer Mannheim GmbH; containing approximately 5% protein) was dissolved in 10 ml of 2N aq. sodium hydroxide. 1 ml of 1.0M silver nitrate was added thereto, and the mixture was autoclaved at 120° C. for 2 hours. This mixture was then diluted with tap water to a predetermined concentration of silver (0.004–0.100 mM), whereby a retentive was obtained.

EXAMPLE 3

Preparation of a retentive composed of a silver compound, tris, and RNA hydrolyzates as starting materials: Preparation 1

0.1 g of yeast-derived RNA (manufactured by Boehringer Mannheim GmbH; containing approximately 5% protein) was dissolved in 10 ml of 2N sodium hydroxide (aq.). To the solution was added 1 ml of 1.0M silver nitrate, and the mixture was then autoclaved at 120° C. for 2 hours. 0.485 ml of this aqueous solution and 50 ml of 200 mM tris were combined, followed by addition of water to adjust the total volume to 1 liter, whereby a retentive (0.040 mM silver and 10 mM tris) was obtained.

EXAMPLE 4

Preparation of a retentive composed of a silver compound, tris, and RNA hydrolyzates as starting materials: Preparation 2

0.2 g of yeast-derived RNA (manufactured by Boehringer Mannheim GmbH; containing 5% protein) was dissolved in 10 ml of 2 N sodium hydroxide (aq.), and the solution was heated at 100° C. for 1 hour, whereby RNA was hydrolyzed. Then, the total volume of the solution was adjusted by addition of water to 26.7 ml, so that solution A was obtained. Separately, 0.21 g of silver nitrate was dissolved in 3.3 ml of 10 mM tris, so that solution B was obtained.

Solution A and solution B were combined and adjusted to pH 6.5 by adding acetic acid, and the mixture was allowed to stand for precipitation. The resulting precipitates were then collected centrifugation (at 3,000 rpm for 15 minutes). The precipitates were dissolved by adding an equal volume of 1M tris. The solution was diluted with tap water to a predetermined concentration of silver (0.004–0.400 mM), whereby a retentive was obtained.

EXAMPLE 5

Preparation of a retentive composed of a silver compound, tris, and RNA hydrolyzates as starting materials: Preparation 3

0.1 g of yeast-derived RNA (manufactured by Boehringer Mannheim BmbH; containing approximately 5% protein) was dissolved in 5 ml of 2N sodium hydroxide (aq.), and the solution was autoclaved at 120° C. for 2 hours. The resultant hydrolyzates were neutralized with acetic acid, then precipitated with ethanol, and centrifuged (3,000 rpm for 10 minutes), whereby the precipitates were collected. The precipitates were dissolved in 5 ml of 0.1M tris, so that solution A was obtained.

Alternatively, 0.17 g silver nitrate was dissolved in 5 ml of 0.1M tris, so that solution B was obtained.

Solution A and solution B were combined (whereby black precipitates were formed) and then autoclaved at 120° C. for 30 minutes, whereby an original solution of retentive was obtained. Before use, the original solution was diluted with water followed by addition of 3–30 mM tris. The foregoing also applies to cases where the primary amine used in place of tris is methylamine, ethylamine, monoethanolamine, 2-amino-2-methyl-1,3-propanediol, 2-amino-2-ethyl-1,3-propanediol, α-aminooxyacetic acid, or aminoethoxyvinylglycine.

EXAMPLE 6

Preparation of a retentive composed of a silver compound, tris, and RNA hydrolyzates as starting materials: Preparation 4

0.1 g RNA derived from yeast was dissolved in 10 ml of 2N sodium hydroxide (aq.). The aqueous solution was subjected to hydrolysis at 100° C. for 1 hour, followed by addition of 16.7 ml water to the resulting hydrolyzates, so that solution A was obtained.

Separately, 0.105 g silver nitrate was dissolved in 3.3 ml water, so that solution B is obtained.

Solution A and solution B were combined, then neutralized with acetic acid, and was centrifuged. The supernatant was precipitated with ethanol, and the resulting precipitates were dissolved in 2 ml of 0.5M tris or dilute alkali, whereby an original solution of retentive was obtained. Before use, the original solution is diluted in the same way as in Example 5. The foregoing also applies to cases where the primary amine used in place of tris is methylamine, ethylamine, monoethanolamine, 2-amino-2-methyl-1,3-propanediol, 2-amino-2-ethyl-1,3-propanediol, α-aminooxyacetic acid, or aminoethoxyvinylglycine.

[Test Examples]

Test Example 1

Effect of retentive on carnation (Test 1)

Retentives containing silver and tris in the concentrations set forth in Table 1 were prepared according to Example 1 and were examined for effect on cut carnation flowers (variety: Red Korso) where one test group consisted of 10 cut flowers. Cut flowers immediately after being harvested in a farm were immersed and allowed to such up water for 4 hours in each retentive. Then, the retentives were discarded and replaced by tap water. On 9 days thereafter, the number of healthy flowers was counted. Results are set forth in Table 1 where the percentages of healthy flowers are shown.

TABLE 1

| Sample | Ag (mM) | Tris (mM) | Number of days after treatment | | | | |
|---|---|---|---|---|---|---|---|
| | | | 5 | 6 | 7 | 8 | 9 |
| Ag-Tris | 0.040 | 3.75 | 100 | 100 | 100 | 100 | 20 |
| Ag-Tris | 0.040 | 7.50 | 100 | 100 | 100 | 60 | 40 |
| Ag-Tris | 0.040 | 18.75 | 100 | 100 | 80 | 40 | 0 |
| Ag-Tris | 0.040 | 60.00 | 100 | 100 | 90 | 0 | 0 |
| Ag-Tris | 0.400 | 12.50 | 100 | 100 | 100 | 80 | 60 |
| Silver nitrate | 0.040 | — | 100 | 60 | 60 | 0 | 0 |
| Silver thiosulfate complex | 0.400 | — | 100 | 100 | 100 | 80 | 60 |
| Tap water | — | — | 60 | 0 | 0 | 0 | 0 |

As is evident from Table 1, the retentives of the present invention demonstrated almost the same effect as that of the silver thiosulfate complex.

Test Example 2

Effect of retentive on carnation (Test 2)

The retentives prepared in Examples 1, 2, and 3 were examined for effect on cut flowers. The flowers examined were carnation whose variety was Shinano Pink. One test group consisted of 10 cut flowers. The states of flowers were evaluated every day and the number of healthy flowers was counted. Results are shown in Table 2.

TABLE 2

| Sample | Ag (mM) | Tris (mM) | Number of days after treatment | | | |
|---|---|---|---|---|---|---|
| | | | 7 | 8 | 9 | 10 |
| Ag-RNA-Tris | 0.040 | 10.0 | 90 | 90 | 90 | 80 |
| AG-RNA | 0.040 | — | 100 | 90 | 60 | 30 |
| Ag-RNA | 0.100 | — | 80 | 70 | 60 | 50 |
| AG-DNA | 0.040 | — | 80 | 60 | 40 | 30 |
| AG-DNA | 0.100 | — | 70 | 60 | 50 | 40 |
| g-Tris | 0.400 | 10.0 | 80 | 50 | 20 | 10 |
| Silver nitrate complex | 0.400 | — | 100 | 100 | 90 | 80 |
| Tap water | — | — | 10 | 0 | 0 | 0 |

RNA: RNA hydrolyzates,
DNA: DNA hydrolyzates.

From Table 2, the following was made evident.

① The retentives composed of silver and a nucleic acid as starting materials exhibited a freshness retentive effect on the flowers.

② The retentive composed of silver, tris, and RNA hydrolyzates as starting materials, which contained approximately 1/10 silver relative to the silver thiosulfate complex, exhibited a freshness retentive effect to the level of the silver thiosulfate complex. In this test example, stains appeared at the top of petals in the test group treated with the silver thiosulfate complex.

Test Example 3

Effect of retentive on carnation (Test 3)

A retentive prepared according to Example 4 was tested (where the concentration of tris was 10 mM). The flowers examined were carnation (variety: Shine). One test group consisted of 5 cut carnation flowers, and the states of the flowers were evaluated every day and the number of healthy flowers was counted. Results are shown in Table 3.

TABLE 3

| Sample | Ag (mM) | Number of days after treatment | | | | | |
|---|---|---|---|---|---|---|---|
| | | 5 | 6 | 7 | 8 | 9 | 10 |
| Ag-RNA-Tris | 0.400 | 100 | 90 | 80 | 70 | 60 | 60 |
| Ag-RNA-Tris | 0.040 | 100 | 100 | 90 | 70 | 60 | 40 |
| Ag-RNA-Tris | 0.004 | 100 | 100 | 90 | 80 | 40 | 20 |
| Silver thiosulfate complex | 0.400 | 100 | 90 | 90 | 80 | 20 | 0 |
| Silver thiosulfate complex | 0.040 | 90 | 40 | 30 | 30 | 30 | 20 |
| Tap water | — | 90 | 40 | 10 | 10 | 0 | 0 |

RNA: RNA hydrolyzates.

From Table 3, the following was made evident with respect to the retentives composed of a silver compound and RNA hydrolyzates as starting materials:

① There was no particular difference between 0.004–0.400 mM silver in respect of the retentive effect.

② Even at a silver concentration of $\frac{1}{10}$–$\frac{1}{100}$ relative to the silver thiosulfate complex, the retentives demonstrated a freshness retentive effect to the level of the silver thiosulfate complex.

Test Example 4

Effect of retentive on carnation (Test 4)

A retentive prepared according to Example 6 was examined for freshness retentive effect on two varieties of carnation (Red Korso and Nora). Each test group consisted of 5 cut flowers. Before the test, the retentive was diluted with water to a silver concentration of 0.026 mM, followed by addition of 5.0, 10.0, and 15.0 mM 2-amino-2-methyl-1,3-propanediol and/or 5.0, 10.0, and 15.0 mM tris. The test was carried out as described in Example 1. Results were shown in Table 4.

TABLE 4

| | Ag (mM) | Tris (mM) | AMP (mM) | Number of days after treatment | | | | |
|---|---|---|---|---|---|---|---|---|
| | | | | 6 | 7 | 8 | 9 | 10 |
| Ag-RNA-Tris | 0.026 | 5.0 | — | 100 | 100 | 100 | 70 | 50 |
| Ag-RNA-Tris | 0.026 | 10.0 | — | 100 | 100 | 100 | 90 | 40 |
| Ag-RNA-Tris | 0.026 | 15.0 | — | 100 | 100 | 100 | 80 | 60 |
| Ag-RNA-Tris | 0.026 | — | 5.0 | 100 | 100 | 70 | 50 | 40 |
| Ag-RNA-Tris | 0.026 | — | 10.0 | 100 | 100 | 100 | 70 | 50 |
| Ag-RNA-Tris | 0.026 | — | 15.0 | 100 | 100 | 90 | 50 | 40 |

TABLE 4-continued

| | Ag (mM) | Tris (mM) | AMP (mM) | Number of days after treatment | | | | |
|---|---|---|---|---|---|---|---|---|
| | | | | 6 | 7 | 8 | 9 | 10 |
| Ag-RNA-Tris | 0.026 | 5.0 | 5.0 | 100 | 100 | 100 | 80 | 50 |
| STS | 0.040 | | | 100 | 100 | 100 | 70 | 60 |
| Tap water | | | | 90 | 70 | 30 | 20 | 10 |

RNA: RNA hydrolyzates;
AMP: 2-Amino-2-methyl-1,3-propanediol.

The silver concentrations were determined by atomic absorption spectrometry.

For dilution, tap water was used.

Table 4 indicates that 2-amino-2-methyl-1,3-propanediol has an freshness retentive effect similar to that of tris.

Test Example 5

Effect of retentive on Gypsophila elegans

Cut flowers of *Gypsophila elegans* were treated with a retentive (containing 15.0 mM tris) prepared according to Example 4. Since evaluation of individual flowers of *Gypsophila elegans* based on their states would be meaningless owing to their inherent shape, they were evaluated based on observation of cut flowers as a whole. The total amount of water absorbed from the 1st day to 5th day of the test was quantitatively measured, and the ratio of cut-flower weight on the 5th day to cut-flower weight on the 1st day was determined. Results are shown in Table 5 (the results of observation are bracketed).

TABLE 5

| Sample | Ag (mM) | Ratio (wt. %) | Amount of water absorbed (g) |
|---|---|---|---|
| Ag-RNA-Tris | 0.400 | 66.8 | 424 |
| [Even on the 5th day, neither withering of flowers nor yellowing of stems was observed]; | | | |
| Ag-RNA-Tris | 0.040 | 64.6 | 533 |
| [Even on the 5th day, neither withering of flowers nor yellowing of stems was observed]; | | | |
| Ag-RNA-Tris | 0.004 | 56.2 | 226 |
| [On the 2nd or 3rd day, the withering of flowers and the yellowing of stems occurred] | | | |
| Silver thiosulfate complex | 0.400 | 62.5 | 262 |
| [On the 4th day, the withering of flowers and the yellowing of stems occurred]; | | | |
| Silver thiosulfate complex | 0.040 | 52.5 | 219 |
| [On the 2nd or 3rd day, the withering of flowers and the yellowing of stems occurred]; | | | |
| Silver thiosulfate complex | 0.004 | 52.0 | 189 |
| [On the 2nd or 3rd day, the withering of flowers and the yellowing of stems occurred] | | | |
| Tap water | — | 50.5 | 148 |
| [On the 2nd or 3rd day, the withering of flowers and the yellowing of stems occurred] | | | |

RNA: RNA hydrolyzates.

Table 5 indicates that the retentive composed of the silver compound, RNA hydrolyzates, and tris as starting materials demonstrates an excellent effect on the freshness retention of the cut flowers; that is, the cut flowers were enjoyable during the period of observation by application of this retentive, even at a silver concentration of approximately $\frac{1}{10}$ relative to the silver thiosulfate complex, and the amount of water absorbed was roughly doubled.

Test Example 6

Effect of retentive on chrysanthemum

Cut and unflowered chrysanthemums were treated with a retentive (with 0.040 mM silver and 15.0 mM tris) prepared according to Example 4. Results are shown in Table 6. The freshness of flowers was evaluated by observation of cut flowers as a whole on the basis of not only the states of flowers but also the advancement of flowering and the states of leaves. The cumulative total amount of water absorbed after the beginning of the test was quantitatively determined, and the weight of flowers was measured (Table 6 shows flower weight expressed in terms of percentage relative to flower weight on the day of treatment.).

TABLE 6

| Sample | Item | Number of days after treatment | | | | | | |
|---|---|---|---|---|---|---|---|---|
| | | 0 | 1 | 3 | 6 | 9 | 12 | 15 |
| Ag-RNA-Tris | Flower (wt. %) | 100 | 106 | 112 | 113 | 110 | 107 | 98 |
| Ag-RNA-Tris | Water (g) | — | — | 728 | 1425 | 2031 | 2454 | 2777 |
| Tap water | Flower (wt. %) | 100 | 107 | 97 | 92 | 88 | 87 | 87 |
| Tap water | Water (g) | — | — | 652 | 929 | 1229 | 1477 | 1741 |

RNA: RNA hydrolyzates.

The results of observation are as follows:

The group, treated with the retentive composed of the silver compound, RNA hydrolyzates, and tris as starting materials, completely flowered around 7 days after the treatment and maintained the sound states of flowers even on the 15th day of the test. Even on the 15th day, the leaves kept the same liveliness as on the day of treatment. On the other hand, the control group treated with water completely flowered mainly on the 7th day and commenced gradual withering mainly after the 12th day to become less worthy of appreciation as cut flowers. The leaves softened on the 3rd day and the withering thereof proceeded as the days passed.

After the 15th day of the test, the immersion solution of the untreated group became cloudy with color (brown or green) owing to nutrients flowed from stems to the solution, whereas the immersion solution of the treated group was not colored.

As is evident from the foregoing, the retentive of the present invention has a freshness retentive effect on even such flowers as chrysanthemum etc., being not liable to aging promotion by ethylene.

Test Example 7

Effect of retentive on rose (Test 1)

A retentive prepared according to Example 5 was examined for effect on cut flowers of rose (Rote Rose). Before use, the retentive was diluted with water to a silver concentration of 0.05 mM, and methylamine, ethylamine, or tris was added as a primary amine to a concentration of 15 mM. One test group consisted of 5 cut rose flowers. The states of flowers were evaluated every day and the number of healthy flowers was counted. Since there was no freshness retentive present for rose, water was used for the control group. Results are shown in Table 7.

TABLE 7

| Pretreatment solution | | Number of days after treatment | | | | | | |
|---|---|---|---|---|---|---|---|---|
| Ag (mM) | Primary amine | 3 | 4 | 6 | 7 | 8 | 9 | 10 |
| 0.05 | Methyl amine | 100 | 100 | 40 | 40 | 20 | 0 | 0 |
| 0.05 | Methyl amine | 100 | 100 | 100 | 100 | 100 | 100 | 80 |
| 0.05 | Tris | 100 | 100 | 100 | 100 | 40 | 20 | 20 |

TABLE 7-continued

| Pretreatment solution | | Number of days after treatment | | | | | | |
|---|---|---|---|---|---|---|---|---|
| Ag (mM) | Primary amine | 3 | 4 | 6 | 7 | 8 | 9 | 10 |
| | Tap water | 100 | 20 | 0 | 0 | 0 | 0 | 0 |

Table 7, indicates that the retentives composed of the silver compound, RNA hydrolyzates, and a primary amine (methyl amine, ethyl amine, or tris) as starting materials exhibited an extremely excellent effect on the freshness retention of cut rose flowers.

Test Example 8

Effect of retentive on rose (Test 2)

A retentive prepared according to Example 5 was examined for preservative effect on 5 varieties of rose (Rote Rose, Tineke, Golden Emblem, Sonia, and Carl Red). The test was carried out according to Test Example 6. Results are shown in Table 8–1 to Table 8–5.

TABLE 8-1

| Variety: Rote Rose | | | | | | |
|---|---|---|---|---|---|---|
| | Number of days after treatment | | | | | |
| | 5 | 6 | 7 | 8 | 9 | 10 |
| Ag-RNA-Tris | 100 | 100 | 100 | 100 | 100 | 100 |
| Tap water | 100 | 0 | 0 | 0 | 0 | 0 |

TABLE 8-2

| | Variety: Tineke | | | | | |
| --- | --- | --- | --- | --- | --- | --- |
| | Number of days after treatment | | | | | |
| | 5 | 6 | 7 | 8 | 9 | 10 |
| Ag-RNA-Tris | 100 | 100 | 100 | 100 | 100 | 100 |
| Tap water | 100 | 100 | 80 | 0 | 0 | 0 |

TABLE 8-3

| | Variety: Golden Emblem | | | | | |
| --- | --- | --- | --- | --- | --- | --- |
| | Number of days after treatment | | | | | |
| | 5 | 6 | 7 | 8 | 9 | 10 |
| Ag-RNA-Tris | 100 | 100 | 100 | 100 | 100 | 100 |
| Tap water | 100 | 100 | 100 | 20 | 20 | 0 |

TABLE 8-4

| | Variety: Sonia | | | | | |
| --- | --- | --- | --- | --- | --- | --- |
| | Number of days after treatment | | | | | |
| | 5 | 6 | 7 | 8 | 9 | 10 |
| Ag-RNA-Tris | 100 | 100 | 100 | 100 | 100 | 80 |
| Tap water | 100 | 60 | 20 | 0 | 0 | 0 |

TABLE 8-5

| | Variety: Carl Red | | | | | |
| --- | --- | --- | --- | --- | --- | --- |
| | Number of days after treatment | | | | | |
| | 5 | 6 | 7 | 8 | 9 | 10 |
| Ag-RNA-Tris | 100 | 100 | 100 | 100 | 100 | 40 |
| Tap water | 100 | 80 | 80 | 0 | 0 | 0 |

From these results, the retentive of the present invention exhibited an extremely excellent effect on the freshness retention of cut rose flowers regardless of the variety to which they belong.

APPLICABILITY TO INDUSTRY

The preservative of the present invention exhibits a freshness retentive effect on ethylene-sensitive cut flowers such as carnation, *Gypsophila elegans*, sweet pea, delphinium, dendrobium, lily, stock, antirrhinum, etc., at a silver concentration lower than a conventional retentive containing the silver thiosulfate complex as an active ingredient, and the effect of the present invention is equal to or higher than that of such a conventional retentive.

Up to now, no effective retentives have been present for cut flowers being low sensitive to ethylene, such as chrysanthemum, rose, orchid, etc., but the present retentive demonstrates a significantly excellent effect, particularly on chrysanthemum and rose.

What is claimed:

1. A freshness retentive of cut flowers, which comprises: (a) a mixture of a silver compound, a primary amine, and a nucleic acid-related substance; (b) a reaction product of a silver compound, a primary amine, and a nucleic acid-related substance; or (c) a mixture of a silver compound, a primary amine, and a nucleic acid-related substance and reaction products thereof.

2. The freshness retentive of claim 1, wherein the silver compound is silver nitrate, silver acetate, or silver phosphate.

3. The freshness retentive of claim 1, wherein the primary amine is selected from the group consisting of methylamine, ethylamine, monoethanolamine, tris(hydroxymethyl)aminoethane, 2-amino-2-methyl-1,3-propane-diol, 2-amino-2-ethyl-1,3-propane-diol, α-aminooxyacetic acid, and aminoethoxyvinylglycine.

4. The freshness retentive of claim 1, wherein the nucleic acid-related substance is an RNA hydrolysate.

5. The freshness retentive of claim 1, wherein the nucleic acid-related substance is selected from the group consisting of nucleic acid base, nucleoside, nucleotide, oligonucleotide, polynucleotide, purine derivative, and pyrimidine derivative.

* * * * *